(12) United States Patent
Potyrailo et al.

(10) Patent No.: US 6,541,264 B1
(45) Date of Patent: Apr. 1, 2003

(54) AROMATIC POLYCARBONATE CHARACTERIZATION

(75) Inventors: Radislav Alexandrovich Potyrailo, Niskayuna, NY (US); John Patrick Lemmon, Delanson, NY (US); Terry Kay Leib, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 175 days.

(21) Appl. No.: 09/692,548

(22) Filed: Oct. 19, 2000

(51) Int. Cl.$^7$ ............................................. G01N 33/44
(52) U.S. Cl. ........................................ 436/85; 436/172
(58) Field of Search ................................. 436/161, 164, 436/172, 85; 422/55, 59, 68.1, 70

(56) References Cited

U.S. PATENT DOCUMENTS

| | | | |
|---|---|---|---|
| 5,776,359 A | 7/1998 | Schultz et al. | |
| 5,985,356 A | 11/1999 | Schultz et al. | |
| 6,034,775 A | 3/2000 | McFarland et al. | |
| 6,045,671 A | 4/2000 | Wu et al. | |
| 6,166,133 A | * 12/2000 | Catsman | 525/462 |
| 6,296,771 B1 | * 10/2001 | Petro | 210/143 |

FOREIGN PATENT DOCUMENTS

| | | |
|---|---|---|
| JP | 08-59975 A | 3/1996 |
| JP | 10-36497 A | 2/1998 |
| WO | WO 99/50335 | 3/1999 |

OTHER PUBLICATIONS

JS Humphrey, Jr., AR Shultz and DBG Jaquiss, Macromolecules, *"Flash Photochemical Studies of Polycarbonate and Related Model Compounds, Photodegradation vs. Photo–Fries Rearrangements"*, vol. 6, pp. 305–314 (1973).

MH Chipalkatti, et al, Polym. Mater. Sci. Eng., *"The Investigation of Thermal Degradation In Polymers By Fluorescence Spectroscopy and potential Applications In Processing"*, vol. 64, pp. 131–132 (1991).

CE Hoyle, H. Shah and GL Nelson, J. Polym. Sci. A., *"Photochemistry of Bisphenol–A Based Polycarbonate: The Effect of the Matrix and Early Detection of Photo–Fries Product Formation"*, vol. 30, pp. 1525–1533 (1992).

S. Pankasem, J. Kuczynski and JK Thomas, Macromolecules, *"Photochemistry and Photodegradation of Polycarbonate"*, vol. 27, pp. 3773–3781 (1994).

H. Shah, IB Rufus and CE Hoyle, Macromolecules, *"Photochemistry of Bisphenol–A–Based Polycarbonate: Early Detection of Photoproducts by Fluorescence Spectroscopy"*, vol. 27, pp. 553–561 (1994).

(List continued on next page.)

Primary Examiner—Jill Warden
Assistant Examiner—Yelena Gakh
(74) Attorney, Agent, or Firm—Andrew J. Caruso; Noreen C. Johnson

(57) ABSTRACT

In a rapid and non-invasive method for characterizing aromatic polycarbonates, fluorescence intensities are determined at least two wavelength ranges and used to calculate a compositional or physical property of the sample. The method is suitable for determining the relative amounts of linear and branched polycarbonates, and it is fast enough to monitor the progress of polymerization reactions.

19 Claims, 11 Drawing Sheets

OTHER PUBLICATIONS

IB Rufus, H. Shah and CE Hoyle, J. App. Polym. Sci., "Identification of Fluorescent Products Produces By the Thermal Treatment of Bisphenol–A–Based Polycarbonate", vol. 51, pp. 1549–1558 (1994).

A. Factor, "Mechanisms of Thermal and Photodegradation of Bispheyl A Polycarbonate", Chapter 5 in RL Clough, et al eds., "Polymer Durability: Degradation, Stabilization, and Lifetime Prediction", American Chemical Society, (1995).

CE Hoyle, IB Rugus and H. Shah, Can. J. Chem., "Solvent Effect On the Photophysics of Bisphenol–A–Based Polycarbonate and Diphenylcarbonate" vol. 73, pp. 2062–2068 (1995).

K. Reihs, et al, Fresnius' J. Anal. Chem., "Molecular Weight Determination of Bulk Polymer Surfaces by Static Secondary Ion Mass Spectrometry", vol. 358, No. 1–2, pp. 93–95 (1997).

* cited by examiner

AROMATIC POLYCARBONATE CHARACTERIZATION

BACKGROUND OF THE INVENTION

The present invention relates to a method for determination of fluorescent products in polymerization reactions. In particular, the invention relates to a method for rapid measurement of fluorescent products in solid and solution polycarbonate samples to provide information about the samples' composition or physical properties.

Aromatic polycarbonates are typically synthesized by reaction of an aromatic diphenol, such as 2,2'-bis(4-hydroxyphenyl)propane (also known as bisphenol A or BPA), with derivatives of carbonic acid, such as phosgene or diphenyl carbonate, in the presence of a catalyst. See, for example, U.S. Pat. No. 3,028,365 to Schnell et al., U.S. Pat. No. 3,334,154 to Kim, U.S. Pat. No. 3,989,672 to Vestergaard, U.S. Pat. No. 4,131,575 to Adelmann et al., and U.S. Pat. No. 5,606,008 to Sakashita et al.; World Patent Application 1999-50335 to Funakoshi et al.; and Japanese Unexamined Patent Publications JP 2000-063507-A, JP 11-005837-A and JP 11-158261-A.

One important property of the synthetic reaction conditions is selectivity for the formation of linear versus branched polycarbonate chains. Product selectivity may be defined as the ratio of the molecular weight (number average molecular weight, $M_n$, or weight average molecular weight, $M_w$) of polycarbonate to the concentration of branched product, also known as Fries product. Formation of Fries product, shown schematically below, can occur through selective catalysis or rearrangement to form a branched polycarbonate.

Scheme

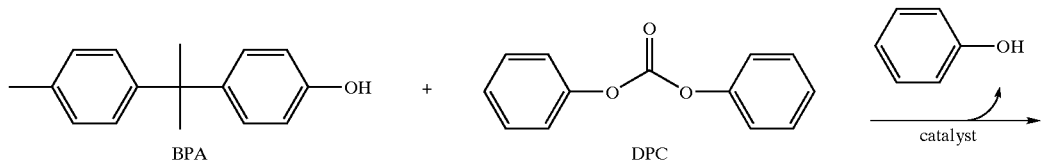

BPA          DPC

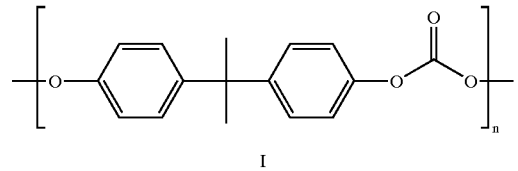

I

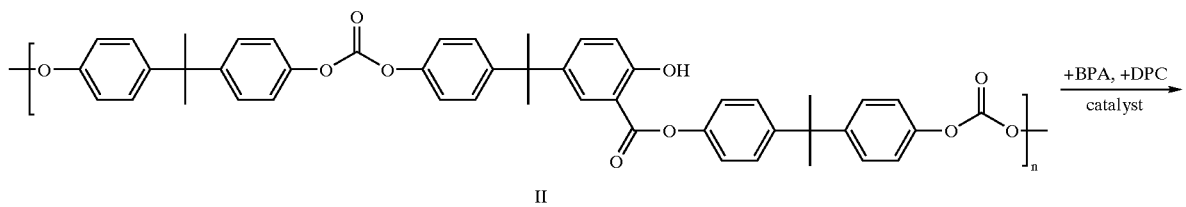

II

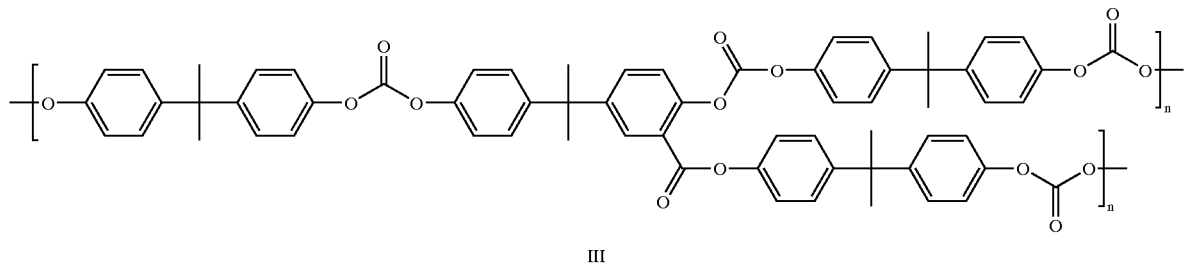

III

The phenyl salicylate product II and the branched polycarbonate III are collectively referred to herein as Fries product. The properties of the product polycarbonate are strongly influenced by the amount of Fries product present, and it is often desirable to minimize the Fries product content for consistent melt flow properties. Therefore, in exploring new reaction conditions for polycarbonate synthesis, it would be useful to employ a rapid and convenient technique for characterizing product selectivity.

Traditional techniques for measurements of polymer molecular weight, such as size-exclusion chromatography and light scattering, require extensive and time-consuming sample preparation steps to dissolve the solid polymer for analysis. See, for example, the techniques described by G. C. Berry in *Concise Encyclopedia of Materials Characterization*, R. W. Cahn and E. Lifshin, eds., Pergamon Press, Oxford England, pages 343–350 (1993); H. G. Barth, *Advances in Chemistry Series*, volume 247, pages 3–11 (1995); and K. Reihs, M. Voetz, M. Kruft, D. Wolany, and A. Benninghoven, *Fresnius' Journal of Analytical Chemistry*, volume 358, pages 93–95 (1997). Similar time-consuming sample preparation is also needed for measurements of Fries product by traditional techniques such as nuclear magnetic resonance (NMR) spectroscopy and high performance liquid chromatography (HPLC). See, for example, A. Factor, "Mechanisms of Thermal and Photodegradation of Bisphenyl A Polycarbonate", Chapter 5 in R. L. Clough et al. eds., "Polymer Durability:

Degradation, Stabilization, and Lifetime Prediction", 1995, American Chemical Society. Thus, molecular weight and Fries analysis by means of known techniques is both time and labor intensive. In addition, these techniques are invasive and destructive of sample.

There accordingly remains a need in the art for a method to rapidly characterize aromatic polycarbonates and thus the product selectivity of reaction conditions. There also remains a need for a method of monitoring product selectivity that is non-destructive and sufficiently rapid to monitor the progress of polycarbonate synthesis reactions in situ.

SUMMARY OF THE INVENTION

A rapid and convenient method for characterizing an aromatic polycarbonate comprises: providing at least one analytical sample comprising an aromatic polycarbonate; irradiating the analytical sample at a first wavelength range to excite fluorescence; detecting fluorescence emission intensities from the analytical sample at least a second wavelength range and a third wavelength range, the second wavelength range and the third wavelength range being separated from each other and from the first wavelength range by at least five nanometers; and characterizing the analytical sample based on the fluorescence emission intensities at the second wavelength range and the third wavelength range.

BRIEF DESCRIPTION OF TEE DRAWINGS

FIGS. 10A–C is a plot of the ratio of fluorescence intensities at 400 and 500 nm (340 nm excitation) versus the ratio of number average molecular weight (in grams/mole) to Fries product content (in parts per million); plots A–C correspond to final processing temperatures of 280, 295 and 310° C., respectively.

FIGS. 11A–F are plots of catalyst selectivity measured by fluorescence and independently by hydrolysis/HPLC versus catalyst concentration at 310° C. measured on solid samples; each data point for the fluorescence data is the mean of three measurements, error bars represent one standard deviation; each plot is for a different catalyst: A, $Cs_2SO_4$; B, $CsH_2PO_4$; C, $CsH_2PO_4$ pH=8.4; D, EDTA monomagnesium disodium pH=6.83; E, $NaH_2PO_3$; F, NaOH.

Figure 12:
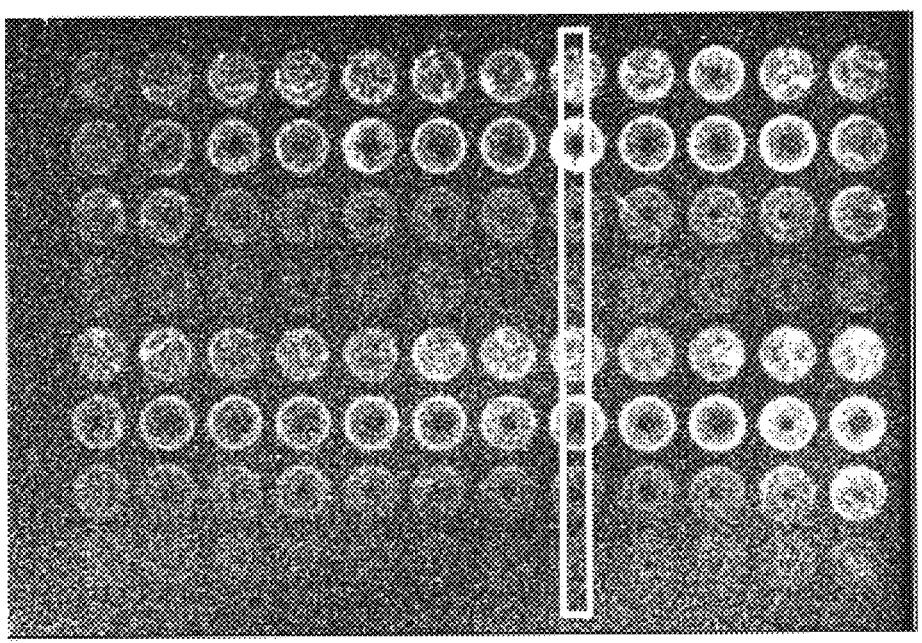

FIG. 12 is a fluorescence image of reaction sites in a catalyst screening experiment; the image was collected with 340 nm excitation and 400 nm emission; the column of sites outlined by the white box was used for comparison of parallel and serial analysis techniques.

Figure 13:
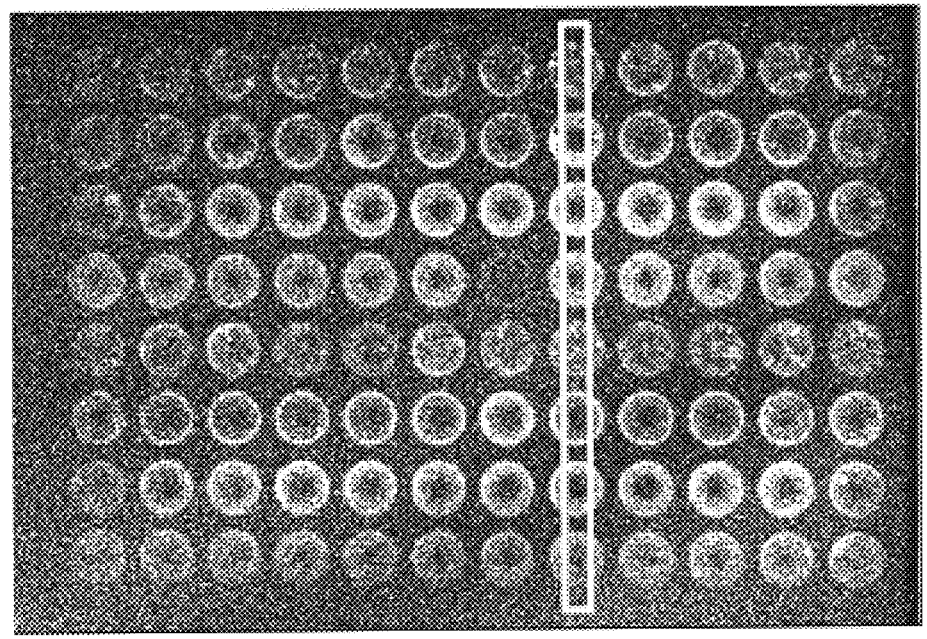

FIG. 13 is a fluorescence image of reaction sites in a catalyst screening experiment; the image was collected with 340 nm excitation and 500 nm emission; the column of sites outlined by the white box was used for comparison of parallel and serial analysis techniques.

Figure 14:
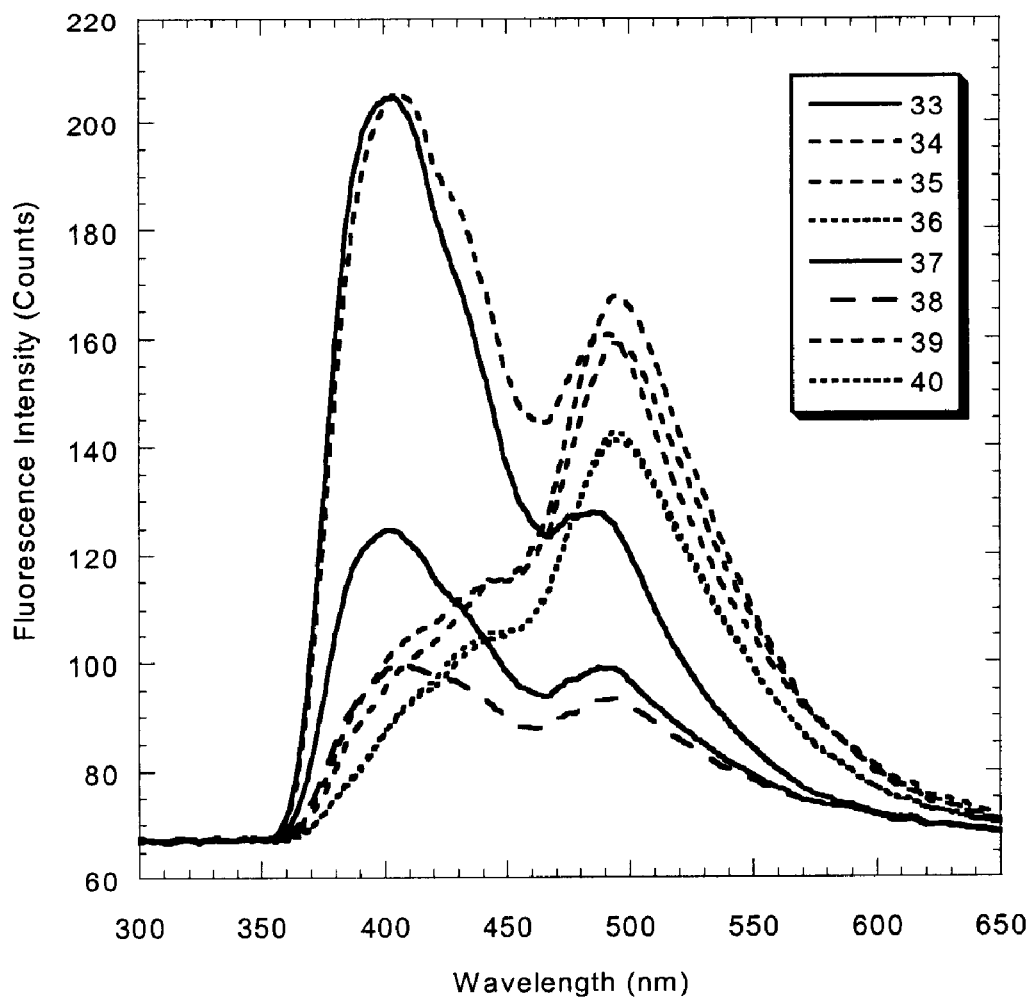

FIG. 14 shows fluorescence spectra of polycarbonate for reaction sites 33 to 40 under the 340 nm excitation wavelength.

Figure 15:
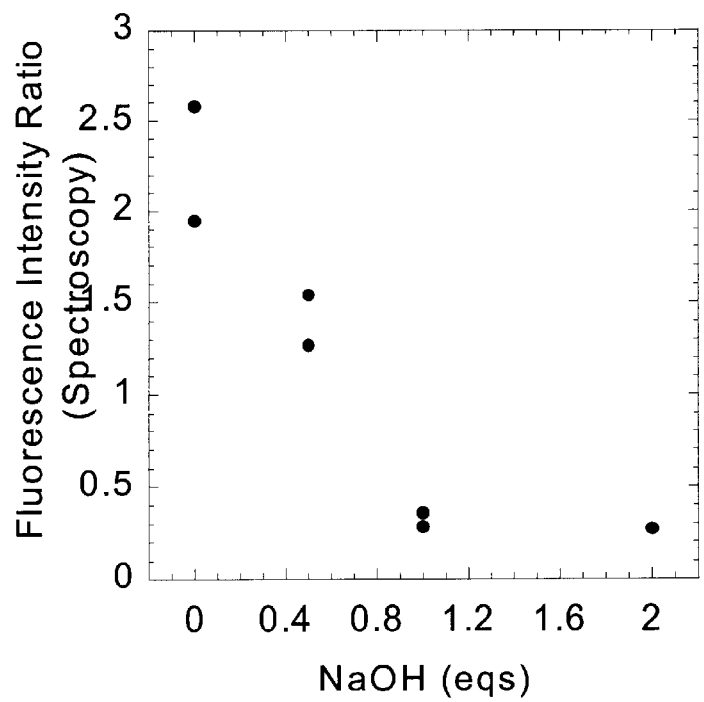

FIG. 15 is a plot of fluorescence intensity ratio ($I_{400}/I_{500}$) as a function of NaOH catalyst loading, where fluorescence intensity ratios were calculated from the fluorescence spectra shown in FIG. 14.

Figure 16:
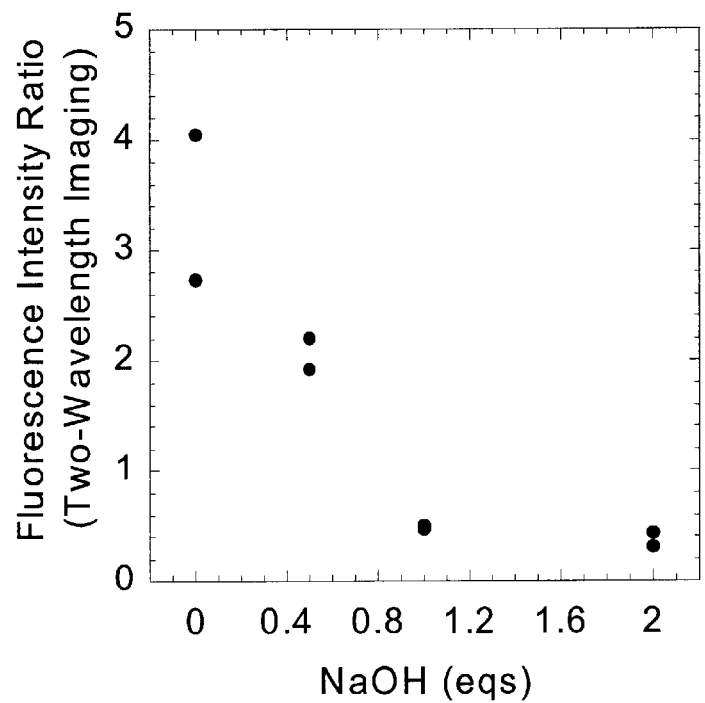

FIG. 16 is a plot of fluorescence intensity ratio ($I_{400}/I_{500}$) as a function of NaOH catalyst loading, where fluorescence intensity ratios were calculated from the fluorescence images shown in FIGS. 12 and 13.

Figure 17:
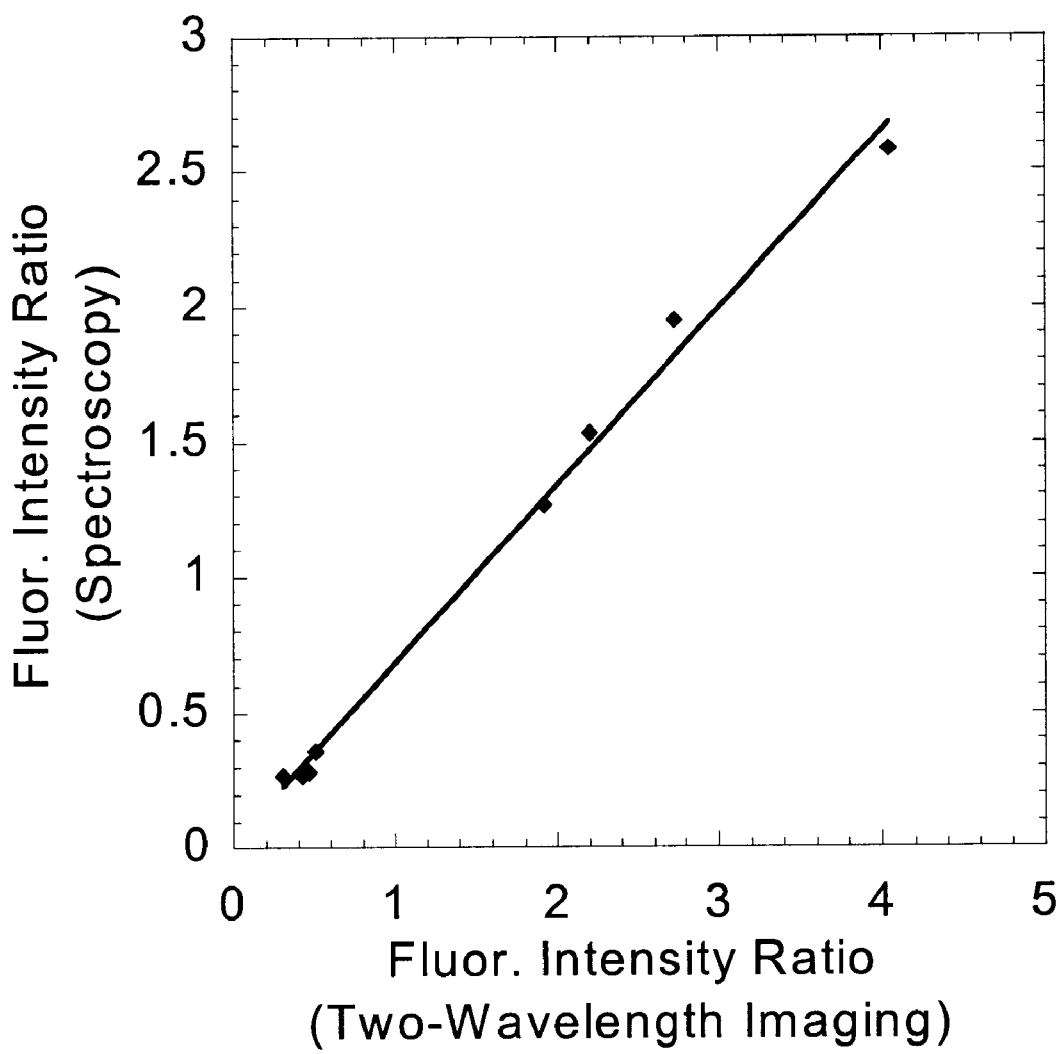

FIG. 17 compares the fluorescence ratio values calculated from the serial and parallel analysis of reaction sites 33 to 40.

DETAILED DESCRIPTION OF THE PREFERRED EMBODIMENTS

A method of characterizing an aromatic polycarbonate comprises: providing at least one analytical sample comprising an aromatic polycarbonate; irradiating the analytical sample at a first wavelength range to excite fluorescence; detecting fluorescence emission intensities from the analytical sample at least a second wavelength range and a third wavelength range, the second wavelength range and the third wavelength range being separated from each other and from the first wavelength range by at least five nanometers; and characterizing the analytical sample based on the fluorescence emission intensities at the second and third wavelength ranges.

The method comprises providing at least one analytical sample comprising an aromatic polycarbonate. Aromatic polycarbonates are a well-known class of polymers and their preparation is described in, among many others, the patents and patent publications to Schnell and others cited in the background section, above. Aromatic polycarbonates comprise repeating units of formula IV:

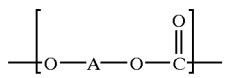

IV wherein A is a divalent aromatic radical derived from a dihydric phenol. The dihydric phenol employed to provide such aromatic polycarbonate polymers is a mononuclear or polynuclear aromatic compounds containing as functional groups two hydroxyl radicals, each of which is attached directly to a carbon atom of an aromatic nucleus. Typical dihydric phenols include 2,2-bis-(4-hydroxyphenyl)-propane (also known as bisphenol A or BPA); hydroquinone; resorcinol; 2,2-bis-(4-hydroxyphenyl)-pentane; 2,4'-dihydroxydiphenylmethane; bis-(2-hydroxyphenyl)-methane; bis-(4-hydroxyphenyl)-methane; bis-(4-hydroxy-5-nitrophenyl)-methane; 1,1-bis-(4-hydroxyphenyl)-ethane; 3,3-bis-(4-hydroxyphenyl)-pentane; 2,2'-dihydroxydiphenyl; 2,6-dihydroxynapthylene; bis-(4-hydroxyphenyl)-sulfone; 2,2'-dihydroxydiphenylsulfone; 4,4'-dihydroxydiphenyl ether; and 4,4'-dihydroxy-2,5-diethoxydiphenyl ether. A variety of additional dihydric phenols are disclosed in U.S. Pat. No. 2,999,835 to Goldberg. It is possible to employ two or more different dihydric phenols, or a dihydric phenol in combination with a glycol, a hydroxy or acid-terminated polyester, or a dibasic acid in order to prepare a carbonate copolymer. Such carbonate copolymers are expressly encompassed by the term "aromatic polycarbonates" as used hereinafter. Preferred phenols include bis-(2-hydroxyphenyl)-methane, 1,1-bis-(4-hydroxyphenyl)-ethane, 2,2-bis-(4-hydroxyphenyl)-propane, and 2,2-bis-(4-hydroxyphenyl)-pentane. A highly preferred phenol is 2,2-bis-(4-hydroxyphenyl)-propane.

The aromatic polycarbonate are prepared by reacting one or more hydric diphenols with a carbonate precursor. The carbonate precursor may be, for example, phosgene or a carbonic acid diester. A preferred carbonic acid diester is diphenyl carbonate. The reaction mixture may comprise a catalyst, such as those described in, for example, Japanese Patent Publication Nos. JP 2000-063507-A, JP 11-005837-A and JP 11-158261-A. As described below, the catalyst should not interfere with the fluorescence measurement.

The reaction may be conducted in the absence of solvent, under so-called melt polymerization conditions. Alternatively, the reaction mixture may comprise at least one solvent. Suitable solvents include benzene, toluene, xylene, ligroine, cyclohexane, methylcyclohexane, chloroform, methylene chloride, carbon tetrachloride, trichloroethylene, dichloroethane, methylacetate, ethylacetate, and mixtures comprising at least one of the foregoing solvents. Benzene, toluene, xylene, dichloromethane, and mixtures comprising at least one of the foregoing solvents are particularly suitable.

The analytical sample comprising an aromatic polycarbonate may be a purified polycarbonate, a polycarbonate reaction mixture or a polycarbonate reaction mixture that has been further treated. The aromatic polycarbonate may be in liquid or solid form. In one embodiment, the analytical sample may comprise all the constituents of a reaction mixture. Methods of delivering reagents to microscale reaction vessels are described in, for example, U.S. Pat. No. 5,846,396 to Zanzucchi et al. U.S. Pat. No. 5,985,356 to Schultz et al., and U.S. Pat. No. 6,045,671 to Wu et al. In another embodiment, the analytical sample may be derived from a solvent-containing reaction mixture by at least partially removing solvent and other volatile components. A substantially solvent-free analytical sample may be analyzed in solid or melted form. It is preferred that the identity and amount of catalyst are such that the catalyst does not interfere with the fluorescence measurement. In other words, it is preferred that the fluorescence excitation-emission wavelengths and intensities of the catalyst do not interfere with excitation or emission of the polycarbonate.

The method may comprise providing a plurality of spatially differentiated analytical samples, each comprising an aromatic polycarbonate. For example, an analytical matrix may be formed by distributing one analytical site into each well of a 96-well plate. The exact number of analytical sites may vary widely, from two to about one million or more sites. For example, U.S. Pat. No. 5,854,684 to Stabile et al. describes analytical matrices comprising at least one million sites arranged in a density of at least about 10 sites per square centimeter, and U.S. Pat. No. 5,840,246 to Demers et al. provides details for a 7.25 square inch analytical matrix comprising 99,856 sites. In a preferred embodiment, the analytical sites are of substantially uniform geometry and are uniformly distributed throughout all or a portion of the analytical matrix.

The method further comprises irradiating the analytical sample at a first wavelength range to excite fluorescence. The selection of a wavelength range for fluorescence excitation will depend on the structure of the at least one dihydric phenol employed in the polymerization reaction, as well as the intended characterization of the analytical sample, which is described in greater detail below. For example, when the dihydric phenol is a bis-(4-hydroxyphenyl)-alkane and the characterization is a determination of the ratio of number average molecular weight to Fries product content, a suitable first wavelength range may comprise one or more wavelengths from about 300 nanometers (nm) to about 370 nm, preferably from about 330 nm to about 350 nm. Apparatus for fluorescence excitation is well known in the art and comprises at least a light source (e.g., a xenon arc lamp) and a wavelength selector (e.g., monochromator). When the method employs a plurality of analytical samples, it is preferred that excitation illumination of each analytical sample be substantially the same. Alternatively, when the method employs a plurality of analytical samples, the excitation illumination may vary from analytical sample to analytical sample as long as differences in illumination are compensated for in the characterization of the samples.

The method further comprises detecting fluorescence emission intensities from the analytical sample at least a second wavelength range and a third wavelength range, the second wavelength range and the third wavelength ranges being separated from each other and from the first wavelength range by at least five nanometers. It is preferred that the second wavelength range and the third wavelength ranges are separated from each other and from the first wavelength range by at least ten nanometers, more preferably at least fifteen nanometers. As for the selection of a first wavelength range for fluorescence excitation, the selection of the second and third wavelength ranges for fluorescence detection will depend on the structure of the at least one dihydric phenol employed in the polymerization reaction, as well as the intended characterization of the analytical sample. For example, when the dihydric phenol is a bis-(4-hydroxyphenyl)-alkane and the characterization is a determination of the ratio of number average molecular weight to Fries product content, a suitable second wavelength range may comprise one or more wavelengths from about 370 nm to about 440 nm, preferably from about 380 nm to about 420 nm, more preferably about 390 nm to about 410 nm; and a suitable third wavelength range may comprise one or more wavelengths from about 460 nm to about 600 nm, preferably from about 480 nm to about 520 nm, more preferably about 490 nm to about 510 nm.

Apparatus for fluorescence detection is well known in the art and comprises at least a wavelength selector and a detector. When the method employs a plurality of analytical samples, it is preferred that an array detector be employed to enable simultaneous detection of fluorescence emission from more than one analytical sample. Examples of suitable array detectors include a charge-coupled device (CCD), a charge-injection device (CID), a photodiode array, or a photodetector array, all of which are readily commercially available. The array detection device preferably has sufficient resolution that each analytical site is uniquely imaged by at least one, preferably at least nine, more preferably at least 25 pixels. Raw data corresponding to detection of each analytical site may be stored temporarily in the detector or immediately transferred to a computer. While other geometries are possible, a conventional geometry that reduces the amount of scattered excitation light involves excitation of the sample and collection of fluorescence emission at less than 180°.

The method further comprises characterizing the analytical sample based on the fluorescence emission intensities at the second and third wavelength ranges. In general, the characterization may comprise determination or prediction of any sample property for which a one-to-one correlation can be established with the fluorescence emissions at the at least second and third wavelength ranges. The characterization may include but is not limited to aspects of the sample's chemical composition or its physical properties. In one embodiment, the characterization comprises determining the progress of a chemical reaction. For example, in a polycarbonate polymerization, the consumption of dihydric phenol may be determined by recording the change of fluorescence signal (intensity or lifetime) under an excitation wavelength region corresponding to the excitation of dihydric phenol. In a another embodiment, the characterization comprises determining a product selectivity. For example, as demonstrated in working examples below, the product selectivity of reaction conditions may be determined according to a correlation with the ratio of the fluorescence emission intensities in the second and third wavelength ranges. In one embodiment of the method, characterization may utilize a correlation that has already been established. In an alternative embodiment, the method further comprises determining such a correlation. In other words, in this alternative embodiment, the method further comprises calibrating the relationship between the analytical sample characterization and the fluorescence emission intensities at the at least second and third wavelength ranges using an independent analytical method. For example, a ratio of emission intensities at the second and third wavelength ranges may be correlated with the ratio of molecular weight to Fries product content, where the molecular weight and Fries product content are determined according to references cited in the background section.

Although the method has been described in terms of fluorescence intensities at a second wavelength range and a third wavelength range, it will be understood that the method may further comprise determining and utilizing fluorescence intensities at additional wavelengths. Time dependent spectroscopies, such as fluorescence lifetimes, may also be employed.

Figure 1:
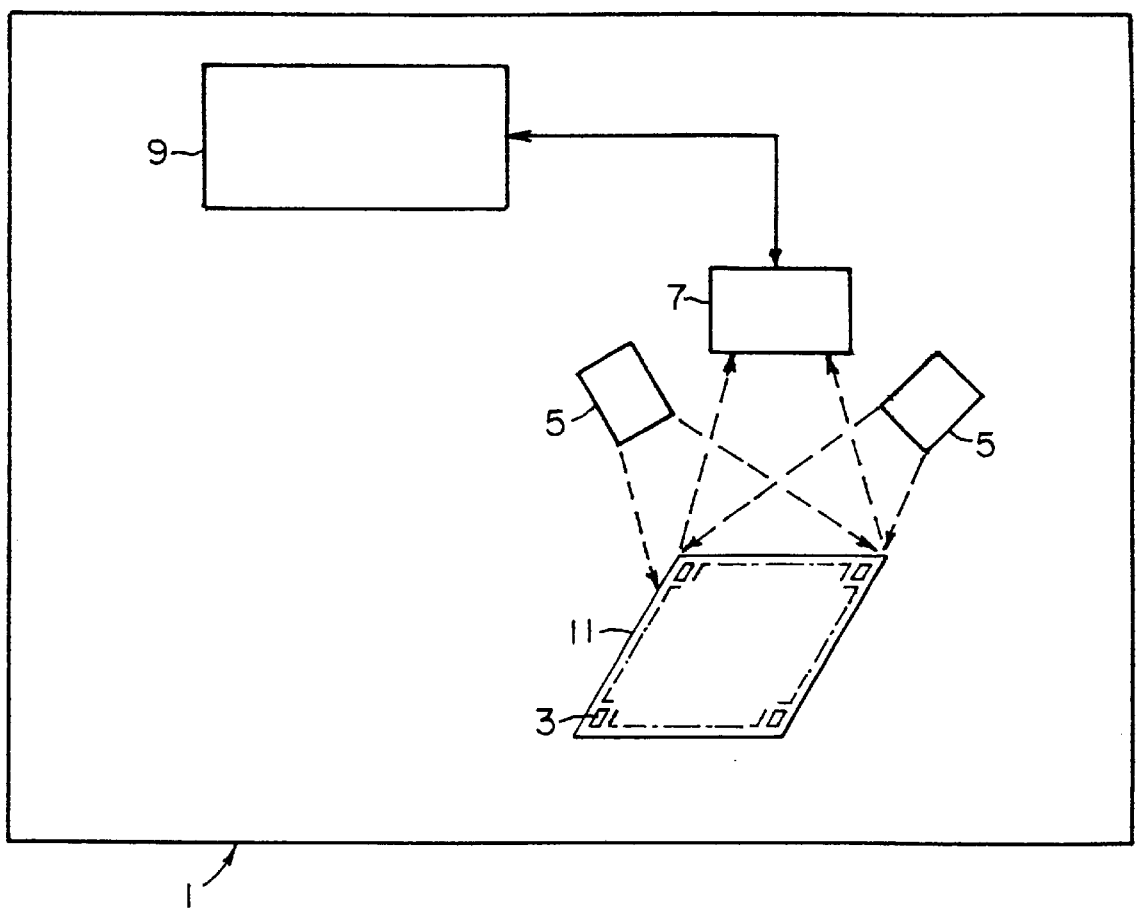
FIG. 1 is a block diagram of a system for characterizing an aromatic polycarbonate.

As illustrated in FIG. 1, the invention further encompasses a system 1 for characterizing an aromatic polycarbonate, comprising: at least one analytical sample 3 comprising an aromatic polycarbonate; one or more light sources 5 for irradiating the analytical sample at a first wavelength range to excite fluorescence; a detector 7 for detecting fluorescence emission intensities from the analytical sample at a second wavelength range and a third wavelength range, the second wavelength range and the third wavelength ranges being separated from each other and from the first wavelength range by at least five nanometers; a computer 9 for characterizing the analytical sample based on the fluorescence emission intensities at the second and third wavelength ranges. When a plurality of analytical samples are provided, they may collectively constitute an analytical matrix 11.

While the invention has been described in terms of characterizing polycarbonate samples with fluorescence spectroscopy, it will be understood that the method and apparatus are more generally applicable to other spectroscopic techniques and sample materials. For example, the method may utilize ultraviolet-visible, infrared, near infrared or Raman spectroscopies. Depending on the property of interest, one or more of the five parameters of a lightwave interacting with a sample can be measured to correlate with the property of interest. These parameters include intensity, wavelength, polarization state, phase, and temporal properties of the lightwave. Likewise, the method is applicable to a wide range of materials and their physical states, including gases, liquids, and solids.

The invention is further illustrated by the following non-limiting examples.

EXAMPLE 1

Number average molecular weights and Fries product contents were determined for a first (calibration) set of twelve samples representing four catalysts, three final (highest) process temperatures, two finishing process times as well as various catalyst concentrations (Table 1). The samples were in a solid state when analyzed. Number average molecular weight ($M_n$) was measured relative to polycarbonate standards using size-exclusion chromatography.

Fries product content was measured by base hydrolysis and high performance liquid chromatographic (HPLC) analysis. Suitable chromatographic techniques for molecular weight and Fries content determination are described in, for example, G. C. Berry in *Concise Encyclopedia of Materials*

Characterization, R. W. Cahn and E. Lifshin, eds., Pergamon Press, Oxford England, pages 343–350 (1993); H. G. Barth, Advances in Chemistry Series, volume 247, pages 3–11 (1995); and K. Reihs, M. Voetz, M. Kruft, D. Wolany, and A. Benninghoven, Fresnius' Journal of Analytical Chemistry, volume 358, pages 93–95 (1997). Product selectivities are given in the last column of Table 1 and expressed as the ratio of number average molecular weight (in grams/mole, abbreviated g/mol) to Fries product content (in parts per million, abbreviated ppm). The product selectivities of these samples span over 2.5 orders of magnitude and range from 1.5 to over 300.

Similar measurements were conducted for a second (validation) set of seven samples, for which results are presented in Table 2.

Dunedin, Fla., Model ST2000). The spectrofluorometer was equipped with a 200 micrometer slit, 600 grooves/mm grating blazed at 400 nm and covering the spectral range from 250 to 800 nm with efficiency greater than 30%, and a linear CCD-array detector. Excitation light from the monochromator was focused into one of the arms of a "six-around-one" bifurcated fiber-optic reflection probe (Ocean Optics, Inc., Model R400-7-UV/VIS). Emission light was collected from a sample when the common end of the fiber-optic probe was positioned near the sample at an angle chosen to minimize the amount of excitation light reflected from the sample back into the probe. The second arm of the probe was coupled to the spectrofluorometer.

Figure 2:
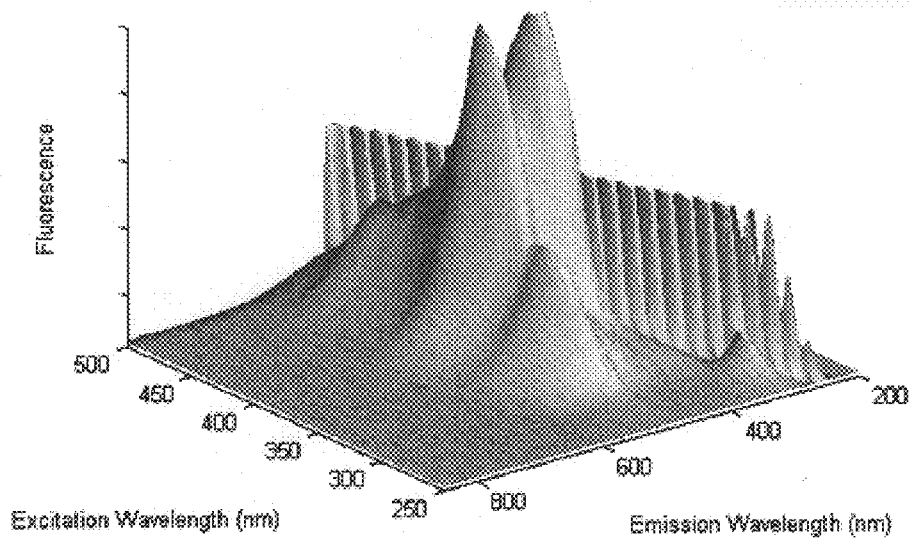
FIG. 2 is a fluorescence excitation-emission map of a solid melt polycarbonate having a ratio of number average molecular weight (in grams/mole) to Fries product content (in parts per million) of 1.5.
Figure 3:
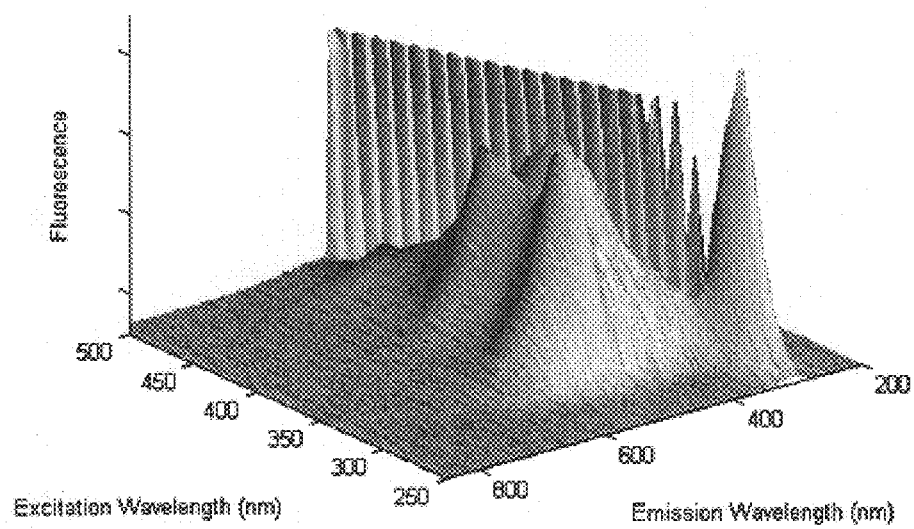
FIG. 3 is a fluorescence excitation-emission map of a solid melt polycarbonate having a ratio of number average molecular weight (in grams/mole) to Fries product content (in parts per million) of 55.4.
Figure 4:
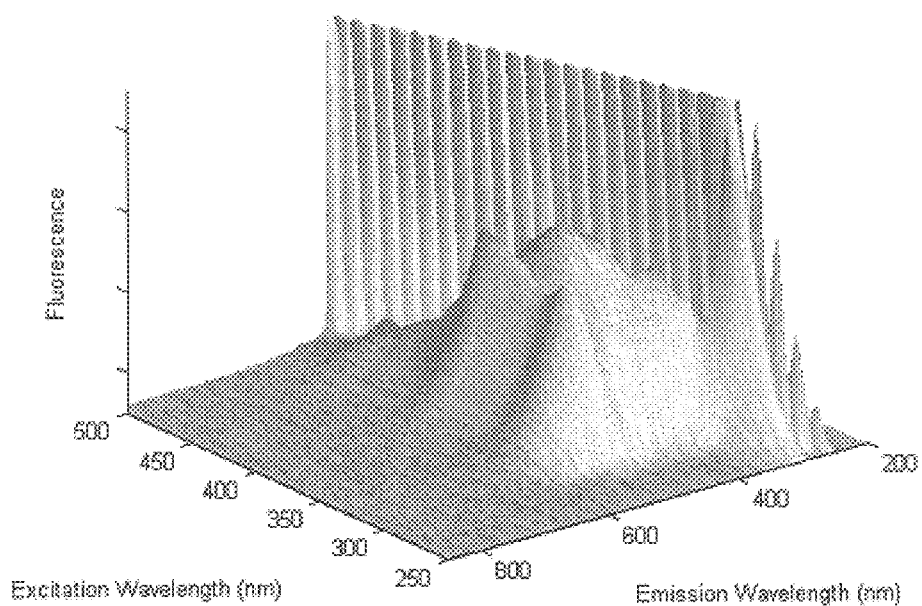
FIG. 4 is a fluorescence excitation-emission map of a solid melt polycarbonate having a ratio of number average molecular weight (in grams/mole) to Fries product content (in parts per million) of 305.8.

These fluorescence excitation-emission maps, provided in FIGS. 2–4, reveal several fluorescent species. Excitation at

TABLE 1

Samples of melt polycarbonate used in initial correlation studies.

| Sample ID | Catalyst | Equivalents | Finishing Processing Temperature (° C.) | Time at Finishing Processing Temperature (min) | $M_n$ (g/mol) | Fries Product (ppm) | $M_n$/Fries |
|---|---|---|---|---|---|---|---|
| 1 | NaOH | 10.51 | 310 | 30 | 8960 | 5985 | 1.497 |
| 2 | NaOH | 10 | 295 | 30 | 8130 | 2996 | 2.714 |
| 3 | NaOH | 10 | 280 | 30 | 7003 | 2110 | 3.319 |
| 4 | $NaH_2PO_3$ | 10 | 310 | 30 | 8924 | 1022 | 8.732 |
| 5 | NaOH | 1.05 | 310 | 30 | 7597 | 471 | 16.13 |
| 6 | $Cs_2SO_4$ | 1.05 | 280 | 30 | 6849 | 242 | 28.3 |
| 7 | $CsH_2PO_4$ | 10 | 280 | 30 | 7290 | 201 | 36.27 |
| 8 | $CsH_2PO_4$ | 1.05 | 310 | 30 | 8487 | 192 | 44.2 |
| 9 | $CsH_2PO_4$ | 0.95 | 280 | 30 | 6591 | 119 | 55.39 |
| 10 | $CsH_2PO_4$ | 10 | 310 | 0 | 5403 | 22 | 245.6 |
| 11 | $CsH_2PO_4$ | 10 | 295 | 0 | 5406 | 20 | 270.3 |
| 12 | $CsH_2PO_4$ | 10 | 280 | 0 | 5505 | 18 | 305.8 |

TABLE 2

Validation samples of melt polycarbonate used in correlation studies.

| Sample ID | Catalyst | Equivalents | Finishing Processing Temperature (° C.) | Time at Finishing Processing Temperature (min) | $M_n$ (g/mol) | Fries Product (ppm) | $M_n$/Fries |
|---|---|---|---|---|---|---|---|
| 13 | $Cs_2SO_4$ | 10.51 | 310 | 30 | 13260 | 4163 | 3.185 |
| 14 | $CsH_2PO_4$ | 13.14 | 295 | 30 | 10933 | 2034 | 5.375 |
| 15 | NaOH | 5.26 | 295 | 30 | 6675 | 1009 | 6.615 |
| 16 | $CsH_2PO_4$ | 5.26 | 310 | 30 | 11267 | 1600 | 7.042 |
| 17 | $NaH_2PO_3$ | 10 | 280 | 30 | 7331 | 356 | 20.59 |
| 18 | $Cs_2SO_4$ | 10.05 | 310 | 30 | 7824 | 249 | 31.42 |
| 19 | NaOH | 1.05 | 295 | 30 | 6463 | 187 | 34.56 |

Figure 5:
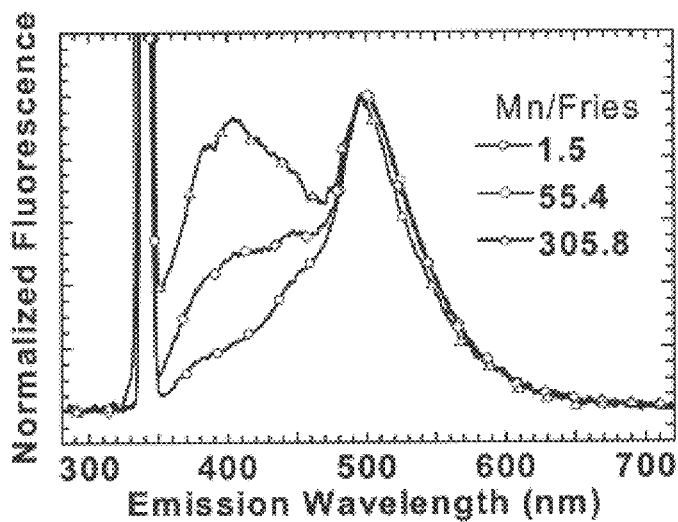
FIG. 5 shows normalized (at 500 nanometers) fluorescence spectra of three solid melt polycarbonate samples having different ratios of number average molecular weight (in grams/mole) to Fries product content. Excitation was at 340 nanometers.

Fluorescence excitation-emission maps were constructed for calibration sample numbers 1 ($M_n$/Fries=1.5), 9 ($M_n$/Fries=55.4), and 12 ($M_n$/Fries=306). Suitable methods for determination of fluorescence-excitation maps are provided in, for example, J. R. Lakowicz, "Principles of Fluorescence Spectroscopy, Second Edition.", Kluwer Academic/Plenum Publishers: New York, N.Y., 1999; and Ingle, J. D., Jr.; Crouch, S. R. Spectrochemical Analysis; Prentice Hall: Englewood Cliffs, N.J., 1988. Measurements were performed on a system which included a white light source (450-W Xe arc lamp, SLM Instruments, Inc., Urbana, Ill., Model FP-024), a monochromator for selection of the excitation wavelength (SLM Instruments, Inc., Model FP-092), and a portable spectrofluorometer (Ocean Optics, Inc., about 280 nanometers (nm) preferentially produces emission at about 300–320 nm, which corresponds to a $\pi$ to $\pi^*$ transition of the carbonyl group in the polycarbonate chain. Excitation over the range from about 300 to about 470 nm produces several emission bands. The strongest have peaks at about 400 and 500 nm. FIG. 5 shows overlaid slices of the excitation-emission maps, corresponding to emission spectra with 340 nm excitation. The fluorescence emission intensities have been normalized at 500 nm, and the spectra show that variations in the independently determined ratio of number average molecular weight to Fries content ($M_n$/Fries) are correlated with the observed ratio of fluorescence intensities at 400 and 500 nm ($I_{400}/I_{500}$).

An initial correlation between the ratio of fluorescence intensities at 400 and 500 nm and the catalyst selectivity was explored using a set of twelve calibration samples (Table 1).

Measurements were performed on the same apparatus used for collection of fluorescence excitation-emission maps.

Figure 6:
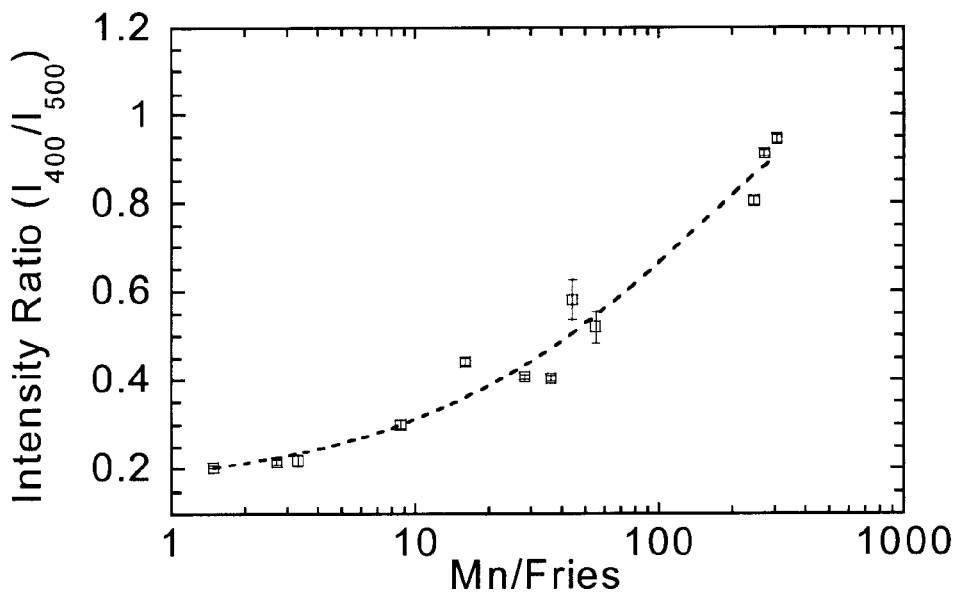
FIG. 6 is a plot, for twelve calibration samples, of the ratio of fluorescence intensities at 400 and 500 nm (340 nm excitation) versus the ratio of number average molecular weight (in grams/mole) to Fries product content (in parts per million).
Figure 7:
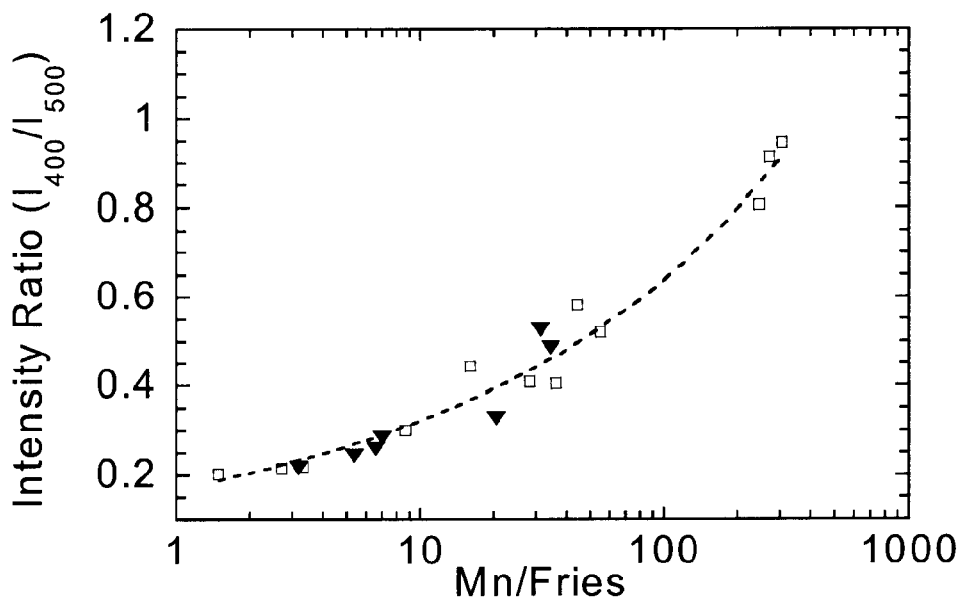
FIG. 7 is a plot, for twelve calibration samples and seven validation samples, of the ratio of fluorescence intensities at 400 and 500 nm (340 nm excitation) versus the ratio of number average molecular weight (in grams/mole) to Fries product content (in parts per million).

The correlation plot is presented in FIG. 6. Measurements on a validation set of samples (Table 2) confirmed the correlation as shown in FIG. 7. The dashed curves in FIGS. 6 and 7 are empirical fits to the equation $$y = m1 - \exp(-m2 x^{m3})$$

where x is the ratio of number average molecular weight to Fries content ($M_n$/Fries), y is the fluorescence intensity ratio ($I_{400}/I_{500}$), and m1, m2 and m3 are empirical fitting parameters.

EXAMPLE 2

Further validation was performed by using another fluorescence instrument to confirm the absence of any instrument-related effects. The second apparatus included a white light source (300 watt Xe lamp, Oriel Instruments, Inc., Stratford, Conn. Model 6258), a 337 nm interference filter (Melles Griot, Inc. Irvine, Calif., Model 03FIU127, 12.4 nm FWHM, 53% peak transmission), a liquid filter to block near-IR radiation (Oriel Instruments, Inc., Model 61945), a spectrograph (Acton Research Corp., Acton, Mass., Model SP150) equipped with a 300 grooves/mm grating blazed at 300 nm, and a charge coupled device (CCD) camera (Roper Scientific, Trenton, N.J., Model TE/CCD 1100 PF/UV). Light from the source was focused into one of the arms of the "six-around-one" bifurcated fiber-optic reflection probe. Emission light was collected from a sample when the common end of the probe was positioned at the sample at an angle chosen to minimize the amount of excitation light reflected from the sample back into the probe. The second arm of the probe was coupled to the spectrograph. The results of the measurements with the second instrument are presented in FIG. 8.

Figure 8:
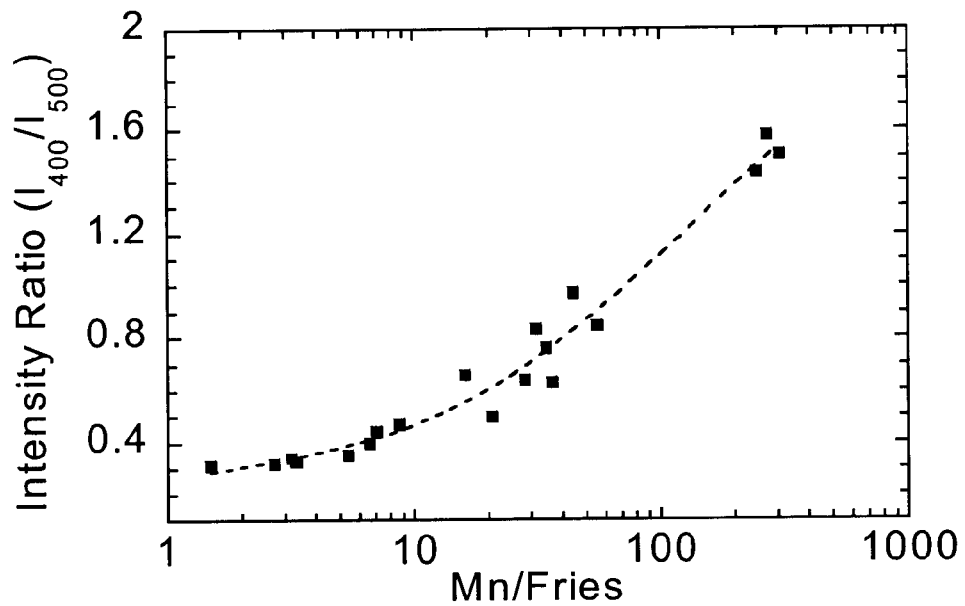
FIG. 8 is a plot, for twelve calibration samples and seven validation samples, of the ratio of fluorescence intensities at 400 and 500 nm (337 nm excitation; CCD detection) versus the ratio of number average molecular weight (in grams/mole) to Fries product content (in parts per million).
Figure 9:
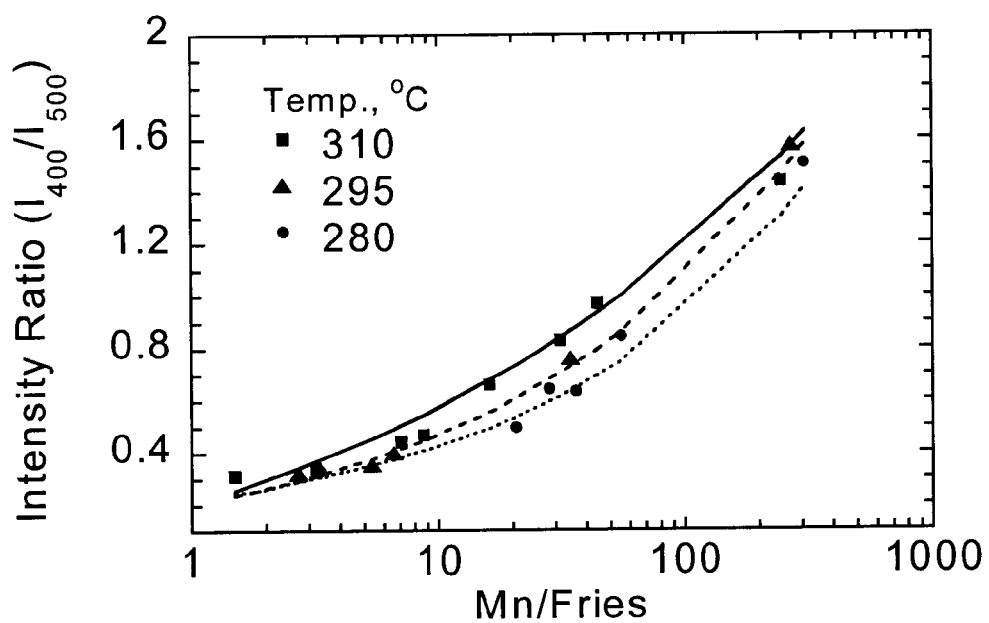
FIG. 9 is a plot of the same data in FIG. 7 except that data points at different finishing processing temperatures are differentiated.

The deviations in the fluorescence ratios from the best fit line over the range of $M_n$/Fries ratios from 10 to 100 were very reproducible in replicated measurements and were essentially apparatus-independent. This observation suggested that one or more experimental parameters might be associated with the deviations. Chemometric analysis of the fluorescence intensity ratio ($I_{400}/I_{500}$) as a function of reaction conditions (as well as independently determined $M_n$/Fries) suggested that processing temperature significantly contributed to this deviation. FIG. 9, in which the same data points used in FIG. 8 are identified according to their corresponding finishing reaction temperature, illustrates the improved ability to predict product selectivity ($M_n$/Fries) when finishing reaction temperature is taken into account. The three best-fit curves in FIG. 9 were calculated using a polynomial fit as in FIG. 8.

EXAMPLE 3

Figure 10:
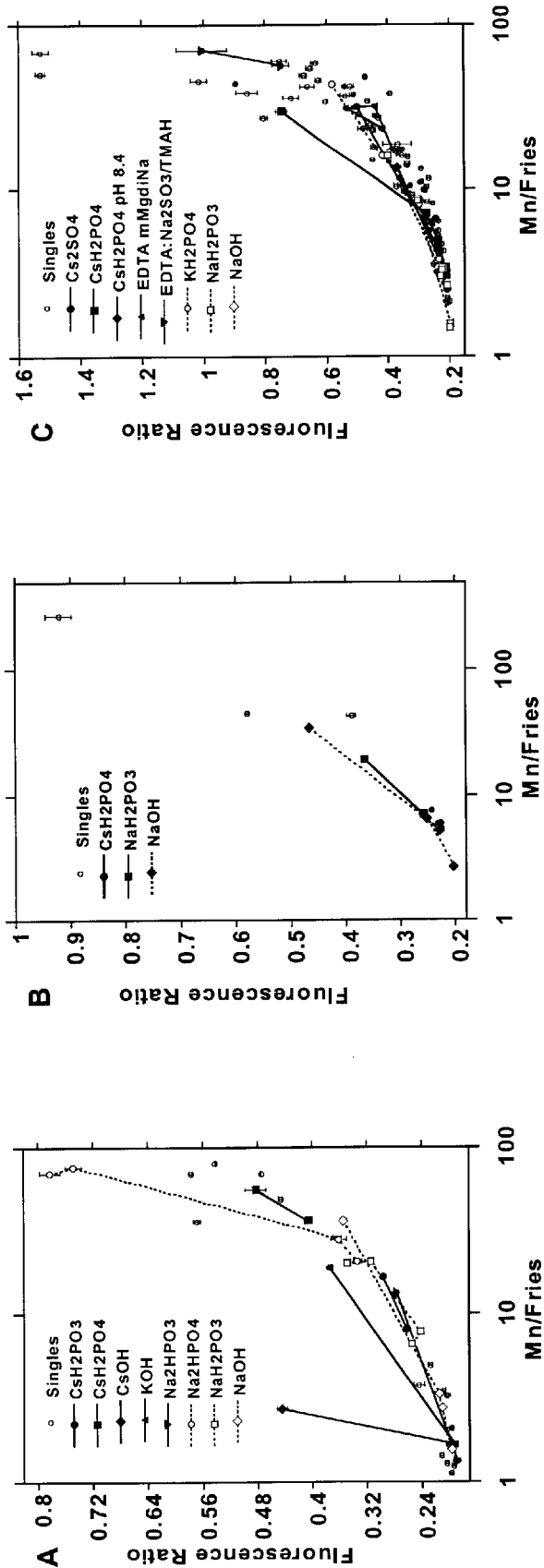
Figure 11:
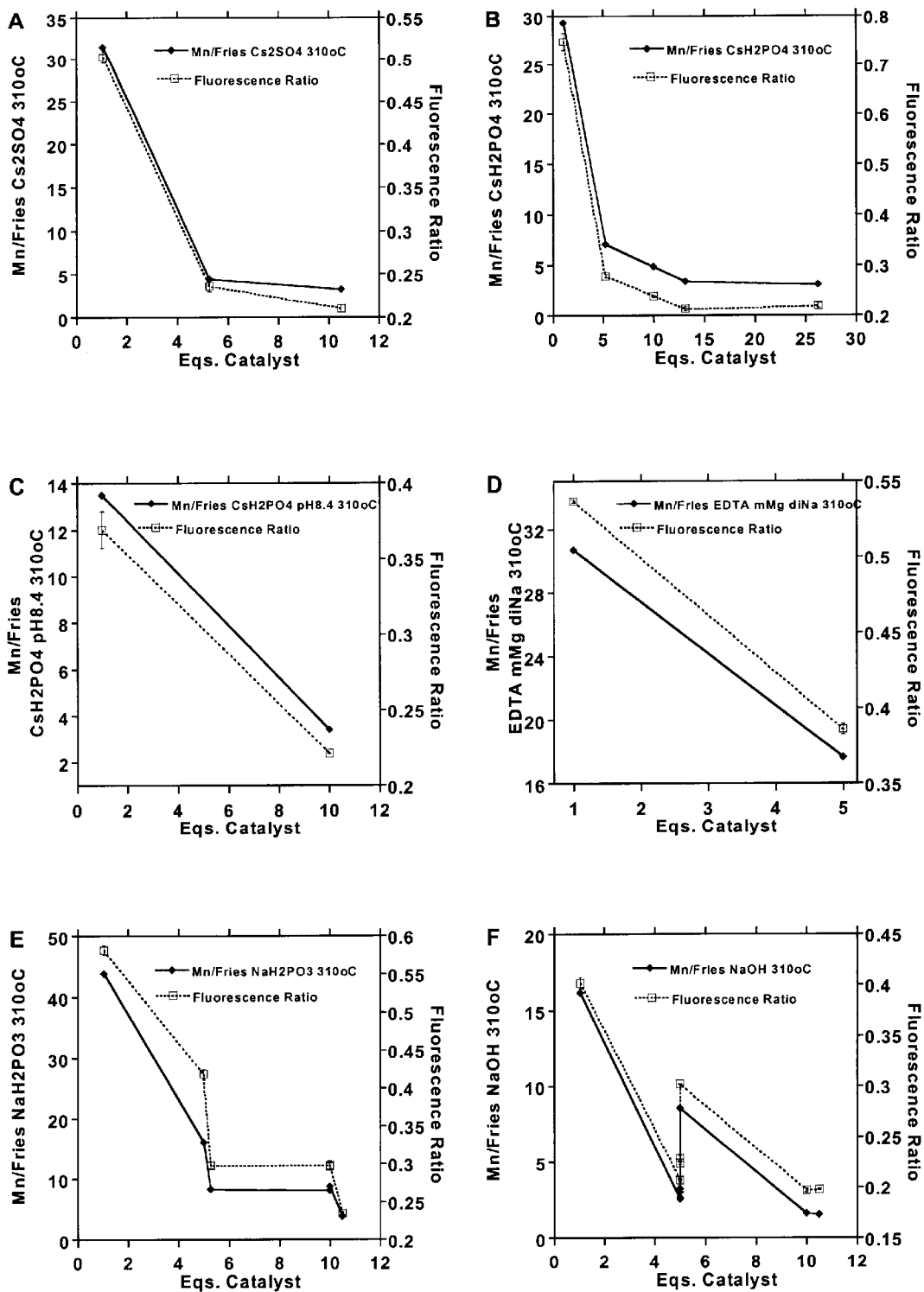

Selectivity measurements for 85 catalysts from a lab-scale reactor were analyzed according to the method of Example 1. The ratio of fluorescence intensities ($I_{400}/I_{500}$) was measured in triplicate for each of the samples. Polymer molecular weight was measured by size exclusion chromatography and Fries products were quantitated by alkaline hydrolysis and RPLC. Plots of ($I_{400}/I_{500}$) vs. independently determined $M_n$/Fries are shown in FIG. 10, where plots A, B, and C correspond, respectively, to reaction temperatures of 280, 295, and 310° C.

It can be seen that all sets of melt polymerization samples with catalysts of different loadings (concentrations) showed good correlation in trends between the independently determined ratio of polymer molecular weight to Fries and the fluorescence intensity ratio. The relative standard deviation (RSD) from the sets of three measurements on each of the samples was in the range from 0.05 to 12.5%. This spread included instrument variability and the inhomogeneity of the measured samples.

For processing temperature of 310° C., FIGS. 11A–11F show the correlation between catalyst selectivity and the ratio of fluorescence intensities at 400 and 500 nm as a function of catalyst loading measured on solid samples. Each data point in the fluorescence data is the mean of three measurements, and error bars represent one standard deviation. Plots A–F represent different catalysts: A, $Cs_2SO_4$; B, $CsH_2PO_4$; C, $CsH_2PO_4$ pH=8.4; D, EDTA monomagnesium disodium pH=6.83; E, $NaH_2PO_3$; F, NaOH. Similar results were found at processing temperatures of 280° C. and 295° C.

EXAMPLE 4

This example demonstrates parallel screening of catalyst selectivity using two-wavelength fluorescence imaging.

The apparatus included a white light source (450 watt xenon arc lamp, SLM Instruments, Inc. Urbana, Ill., Model FP-024), a monochromator for selection of the excitation wavelength (SLM Instruments, Inc. Model FP-092), a quartz lens to expand the light beam from the monochromator for the efficient illumination of the library with the excitation light, a charge coupled device (CCD) camera (Roper Scientific, Trenton, N.J., Model TE/CCD 1100 PF/UV), two interference optical filters for selection of emission wavelengths for fluorescence imaging (400 nm filter (400 nm center wavelength, 10.5-nm half-bandwidth) and 500 nm filter (500.3 nm center wavelength, 8.9 nm half-bandwidth), Ealing Electro-Optics, Inc., Holliston, Mass.), and associated computers for control of the monochromator and CCD camera. For comparison of spectral ratios, fluorescence spectra were also collected using the apparatus described in Example 1 (this technique, which analyzes one reaction site at a time, is referred to as a "serial" technique to distinguish it from parallel analysis of a plurality of sites).

For the validation of the parallel screening method a set of polycarbonate materials was synthesized in the 96-reactor array. A reactant solution (about 100 microliter comprising about 50 mg of total reactants) was loaded into each reaction well and the solvent was evaporated. The reactants were diphenylcarbonate, bisphenol-A, and a relevant catalyst package with sodium hydroxide concentrations ranging from 0 to $2 \times 10^{-4}$ mole per mole BPA.

Fluorescence images collected under a 340-nm excitation through the 400- and 500-nm interference filters are presented in FIGS. 12 and 13. Image size was 483 by 330 pixels for the entire 96-well reactor array (96 reaction sites). The columns highlighted in FIGS. 12 and 13 by white vertical boxes (size of 5 by 330 pixels) correspond to reaction sites 33–40 and were selected for the comparison of the parallel imaging technique with the serial spectroscopic analysis of reaction sites. For quantitation, intensities of respective pixels in columns 293 to 297 were averaged.

FIG. 14 presents the fluorescence spectra of polycarbonate in reaction sites 33 to 40 under the 340-nm excitation wavelength.

FIG. 15 plots the fluorescence intensity ratio values as a function of sodium hydroxide catalyst loading. These values were calculated as the ratio of fluorescence intensities at 400 nm and 500 nm obtained from the fluorescence spectra shown in FIG. 14.

FIG. 16 plots the results of the image analysis that provide the fluorescence intensity ratio values as a function of NaOH catalyst loading. These values were calculated as the ratio of fluorescence intensities at 400 nm and 500 nm obtained from the fluorescence images shown in FIGS. 12 and 13.

FIG. 17 compares the fluorescence ratio values calculated from the serial and parallel spectroscopic analysis of reaction sites 33 to 40. A significant and useful linear correlation exists between the serial and parallel high throughput spectroscopic analysis tools. The correlation does not possess a slope of unity because of a variety of instrumental differences between the spectroscopic and imaging systems. These differences include variable transmission of different interference filters, chromatic aberrations of the used lens and other well-known effects. Once the correlation between two systems is established, the quantitation of catalysts selectivity is performed on both systems interchangeably.

The correlation between employed spectroscopic and imaging measurement systems had a correlation coefficient R=0.997. The slope of the correlation was 0.65 and the intercept was 0.033.

Table 3 compares the fluorescence ratio values calculated from the serial and parallel spectroscopic analysis of reaction sites 33 to 40 after compensation for the instrumental differences.

TABLE 3

| | ($I_{400}/I_{500}$) | |
| --- | --- | --- |
| analytical site | serial analysis | parallel analysis |
| 33 | 2.58 | 2.68 |
| 34 | 1.53 | 1.48 |
| 35 | 0.28 | 0.34 |
| 36 | 0.27 | 0.23 |
| 37 | 1.94 | 1.82 |
| 38 | 1.26 | 1.28 |
| 39 | 0.36 | 0.36 |
| 40 | 0.27 | 0.31 |

While preferred embodiments have been shown and described, various modifications and substitutions may be made thereto without departing from the spirit and scope of the invention. Accordingly, it is to be understood that the present invention has been described by way of illustration and not limitation.

All cited patents and other references are incorporated herein by reference.

What is claimed is:

1. A method of characterizing an aromatic polycarbonate prepared by a "melt" polymerization, said method comprising:

providing at least one analytical sample comprising an aromatic polycarbonate;

irradiating the analytical sample at a first wavelength range to excite fluorescence;

detecting fluorescence emission intensities from the analytical sample at a second wavelength range and a third wavelength range, the second wavelength range and the third wavelength ranges being separated from each other and from the first wavelength range by at least five nanometers; and characterizing the polycarbonate comprising the analytical sample based on the fluorescence emission intensities at the second and third wavelength ranges, said characterizing comprising determining a polycarbonate product selectivity for the "melt" polymerization, wherein the product selectivity for the "melt" polymerization is expressed as the ratio of the polycarbonate number average molecular weight to Fries product content.

2. The method of claim 1, wherein the aromatic polycarbonate is derived from at least one dihydric phenol comprising a bis-(4-hydroxyphenyl)alkane.

3. The method of claim 2, wherein the least one dihydric phenol comprises 2,2'-bis-(4-hydroxyphenyl)propane.

4. The method of claim 1, wherein a plurality of analytical samples are provided.

5. The method of claim 4, wherein the detection of fluorescence emission intensities at the second wavelength range and the third wavelength range is accomplished with an array detector.

6. The method of claim 1, wherein the analytical sample comprises an organic solvent.

7. The method of claim 6, wherein the organic solvent is selected from the group consisting of benzene, toluene, xylene, ligroine, cyclohexane, methylcyclohexane, chloroform, methylene chloride, carbon tetrachloride, trichloroethylene, dichloroethane, methylacetate, ethylacetate, and mixtures comprising at least one of the foregoing.

8. The method of claim 1, wherein the analytical sample is substantially free of organic solvent.

9. The method of claim 8, wherein the analytical sample comprises the aromatic polycarbonate in solid form.

10. The method of claim 8, wherein the analytical sample comprises the aromatic polycarbonate in melted form.

11. The method of claim 1, wherein the first wavelength range comprises one or more wavelengths from about 300 nm to about 370 nm.

12. The method of claim 11, wherein the first wavelength range comprises one or more wavelengths from about 330 nm to about 350 nm.

13. The method of claim 1, wherein the first wavelength range comprises one or more wavelengths from about 380 nm to about 440 nm.

14. The method of claim 13, wherein the first wavelength range comprises one or more wavelengths from about 380 nm to about 420 nm.

15. The method of claim 1, wherein the first wavelength range comprises one or more wavelengths from about 460 nm to about 600 nm.

16. The method of claim 15, wherein the first wavelength range comprises one or more wavelengths from about 480 nm to about 520 nm.

17. The method of claim 1, wherein the characterizing the analytical sample comprises determining the progress of a chemical reaction.

18. A method of characterizing an aromatic polycarbonate prepared by a "metal polymerization, said method comprising:

providing at least one analytical sample comprising an aromatic polycarbonate derived from at least one dihydric phenol comprising 2,2'-bis-(4-hydroxyphenyl) propane;

irradiating the analytical sample at a first wavelength range to excite fluorescence, the first wavelength range comprising one or more wavelengths from about 330 nm to about 350 nm;

detecting fluorescence emission intensities from the analytical sample at a second wavelength range comprising one or more wavelengths from about 380 nm to about 420 nm;

detecting fluorescence emission intensities from the analytical sample at a third wavelength range comprising one or more wavelengths from about 480 nm to about 520 nm; and determining a polycarbonate product selectivity for the "melt" polymerization of the polycarbonate comprising the analytical sample based on the fluorescence emission intensities at the second and third wavelength ranges, wherein the product selectivity is expressed as the ratio of number average molecular weight to Fries product content.

19. The method of claim 18, wherein the product selectivity comprises a measure of branched polymer content in the aromatic polycarbonate.

* * * * *